United States Patent
Nishigishi

(10) Patent No.: US 9,925,078 B2
(45) Date of Patent: Mar. 27, 2018

(54) STENT DELIVERY SYSTEM

(71) Applicant: ASAHI INTECC CO., LTD., Nagoya-shi, Aichi (JP)

(72) Inventor: Makoto Nishigishi, Owariasahi (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 130 days.

(21) Appl. No.: 14/737,989

(22) Filed: Jun. 12, 2015

(65) Prior Publication Data

US 2016/0151183 A1 Jun. 2, 2016

(30) Foreign Application Priority Data

Nov. 29, 2014 (JP) .................................. 2014-242633

(51) Int. Cl.
*A61F 2/966* (2013.01)
*A61F 2/90* (2013.01)
*A61F 2/95* (2013.01)

(52) U.S. Cl.
CPC ................ *A61F 2/966* (2013.01); *A61F 2/90* (2013.01); *A61F 2002/9534* (2013.01); *A61F 2002/9665* (2013.01); *A61F 2230/0091* (2013.01)

(58) Field of Classification Search
CPC .... A61F 2/966; A61F 2/90; A61F 2230/0091; A61F 2002/9665; A61F 2002/9534; A61F 2002/9505; A61B 5/6851; A61B 2017/22042; A61M 25/09;
(Continued)

(56) References Cited

U.S. PATENT DOCUMENTS

| 5,797,857 A * | 8/1998 | Obitsu ................. A61M 25/09 600/585 |
| 5,924,998 A * | 7/1999 | Cornelius ............. A61M 25/09 600/585 |
| 6,833,033 B1 | 12/2004 | Knight |

(Continued)

FOREIGN PATENT DOCUMENTS

| EP | 1 374 801 A1 | 1/2004 |
| EP | 1 374 801 B1 | 4/2006 |

(Continued)

OTHER PUBLICATIONS

Mar. 22, 2016 Extended European Search Report issued in European Application No. 15173337.5.

*Primary Examiner* — Jocelin Tanner
(74) *Attorney, Agent, or Firm* — Oliff PLC

(57) ABSTRACT

A stent delivery system includes a pusher guide wire for delivering a stent having an anchor member. The pusher guide wire includes a core shaft, a coil body that is disposed around a distal portion of the core shaft and includes a tapered portion having an outer diameter that decreases toward a distal end of the coil body, and a protruded portion fixed to the coil body at a position distal to the tapered portion. The anchor member is positioned between the tapered portion and the protruded portion when the stent is delivered using the pusher guide wire. The anchor member can therefore be pushed in the distal direction by the tapered portion of the coil body. Moreover, the stent can be retracted into the catheter by pulling the pusher guide wire in the proximal direction so that the protruded portion contacts the anchor member.

6 Claims, 5 Drawing Sheets

(58) Field of Classification Search
CPC .... A61M 25/0102; A61M 2025/09008; A61M 2025/09083; A61M 2025/09133
See application file for complete search history.

(56) References Cited

U.S. PATENT DOCUMENTS

| | | | | |
|---|---|---|---|---|
| 6,960,227 | B2* | 11/2005 | Jones | A61F 2/95 623/1.11 |
| 7,201,769 | B2 | 4/2007 | Jones et al. | |
| 2003/0083622 | A1* | 5/2003 | Osawa | A61M 25/09 604/164.13 |
| 2005/0246008 | A1* | 11/2005 | Hogendijk | A61F 2/88 623/1.11 |
| 2006/0036309 | A1* | 2/2006 | Hebert | A61F 2/95 623/1.11 |
| 2007/0255385 | A1* | 11/2007 | Tenne | A61F 2/95 623/1.11 |
| 2009/0270974 | A1 | 10/2009 | Berez et al. | |
| 2009/0306760 | A1* | 12/2009 | Hebert | A61F 2/91 623/1.12 |
| 2010/0185271 | A1* | 7/2010 | Zhang | A61F 2/915 623/1.11 |
| 2011/0152791 | A1* | 6/2011 | Kobayashi | A61L 29/085 604/265 |
| 2013/0066413 | A1* | 3/2013 | Jin | A61B 17/12118 623/1.12 |
| 2013/0110000 | A1* | 5/2013 | Tully | A61M 25/09 600/585 |

FOREIGN PATENT DOCUMENTS

| | | |
|---|---|---|
| EP | 2 543 345 A1 | 1/2013 |
| JP | 45-74131 B2 | 11/2010 |
| JP | 2013-521022 A | 6/2013 |

* cited by examiner

STENT DELIVERY SYSTEM

CROSS REFERENCE TO RELATED APPLICATION

This application claims priority to Japanese Application No. 2014-242633 filed on Nov. 29, 2014, the content of which is incorporated by reference herein in its entirety.

BACKGROUND

The disclosed embodiments relate to a medical device. Specifically, the disclosed embodiments relate to a stent delivery system for delivering a stent stored in a catheter to a target site with a pusher guide wire.

Stents are medical devices used at the site of a stenosis or an occlusion created to treat an aneurysm (hereinafter referred to as a "target site") formed in a blood vessel or a digestive organ. For example, a stent may be used for supporting the lumen of a blood vessel or a digestive organ so that the blood vessel or the digestive organ, which is expanded with a balloon catheter, will not be affected with stenosis again. Further, a stent may be used for confining an embolization coil in an aneurysm formed in an arterial blood vessel of the abdomen or the brain to prevent the aneurysm from rupturing.

Stents are generally classified into two categories: a balloon-expandable stent, which is expandable with a balloon catheter, and a self-expandable stent in which the stent expands spontaneously when no longer constrained. Recently, self-expandable stents that are resistant to deformation even when subjected to external force have been often used.

Known stent delivery systems for delivering a stent stored inside a catheter to a target site include a system in which an anchor member provided in a stent is disposed within a gap formed between a middle columnar member and a proximal end columnar member in order to push the stent in the distal direction (for example, see Japanese Patent No. 4574131). In another known stent delivery system, a metal ring is separately provided at the outer periphery of a coil body of a pusher guide wire in order to push a stent in the distal direction (for example, see Japanese Patent Laid-Open Application No. 2013-521022). However, there are problems with each of these stent delivery systems.

As discussed above, the proximal end columnar member of Japanese Patent No. 4574131 can contact the anchor member to deliver the stent in the distal direction when an operator pushes the pusher guide wire in the distal direction. However, the rotating force of the pusher guide wire is difficult to transmit to the distal end of the pusher guide wire when the operator rotates the pusher guide wire, because the middle columnar member is separate from the proximal end columnar member. As a result, it is difficult to precisely release the stent at the target site (in other words, the stent is easily anteroposteriorly dislocated from the target site).

Further, there has been the following problem with the stent delivery system according to Japanese Patent Laid-Open Application No. 2013-521022. Although the rotating force exerted by an operator can be transmitted to the distal end of the pusher guide wire since the coil body of the pusher guide wire is formed as one integral part extending toward the distal end, the flexibility of the pusher guide wire is impaired since the metal ring for pushing the stent in the distal direction is separately provided. In particular, the metal ring may get caught within the catheter when the stent delivery system is inserted into a curved blood vessel or digestive organ, making it difficult to deliver the stent to the target site.

SUMMARY

The disclosed embodiments were devised in view of the above problems. An object of the disclosed embodiments is to provide a stent delivery system in which the flexibility of a pusher guide wire is not impaired, and yet a rotating force exerted by an operator can be transmitted to the distal end of the pusher guide wire, allowing the stent to be easily and precisely released at a target site.

The above problems are addressed by the arrangements listed below.

The disclosed embodiments include a stent delivery system for delivering a stent having an anchor member to a target site with a pusher guide wire. The pusher guide wire comprises a core shaft; a coil body that covers a distal portion of the core shaft and that includes a tapered portion having an outer diameter that decreases toward a distal end of the core shaft; and a protruded portion fixed to the coil body. The protruded portion is fixed to the coil body at a position distal to the tapered portion, and is capable of contacting the anchor member. When the stent is delivered with the pusher guide wire, the anchor member is positioned between the tapered portion and the protruded portion of the coil body.

In this configuration, the flexibility of the pusher guide wire is not impaired since the anchor member can be pushed in the distal direction with the tapered portion of the coil body without requiring a separate metal ring. Further, a rotating force exerted by an operator can be transmitted to the distal end of the pusher guide wire since the coil body extends continuously to the distal end of the pusher guide wire. Moreover, the stent can be retracted into the catheter in the middle of the release process by pulling the pusher guide wire in the proximal direction so that the protruded portion contacts the anchor member. This reduces the risk that the pusher guide wire will get caught inside the catheter when the stent delivery system is inserted into a curved blood vessel or digestive organ, and the stent can be more easily released at the intended target site.

The anchor member may be inclined at the same angle as the tapered portion of the coil body relative to a longitudinal axis of the core shaft. In this configuration, the tapered portion of the coil body can contact a greater surface area of an outer periphery of the anchor member when an operator pushes the pusher guide wire in the distal direction. As a result, even when the stent delivery system is inserted into a curved blood vessel or digestive organ, the stent can be easily delivered to the target site with the pusher guide wire.

The stent delivery system may include a resin layer provided on the outer periphery of the tapered portion. This reduces the risk that the anchor member will get caught between wires of the coil body when an operator pushes the pusher guide wire in the distal direction. As a result, the stent can be more reliably delivered to the target site.

The protruded part may be fixed to an outer periphery of the coil body, or may join a distal end of the core shaft to a distal end of the coil body, thus simultaneously functioning as a distal end joining portion.

BRIEF DESCRIPTION OF THE DRAWINGS

Each of FIGS. 1A-1C shows an overall view of a stent delivery system according to the disclosed embodiments.

DETAILED DESCRIPTION OF EMBODIMENTS

A stent delivery system 1 according to the disclosed embodiments is described with reference to FIGS. 1A to 1C and FIG. 2. In FIGS. 1A to 1C and FIG. 2, as well as in FIGS. 3 to 5, the left side corresponds to the distal end (the front end), which is to be inserted into the body, and the right side corresponds to the proximal end (the base end), which is to be operated by an operator such as a physician. Note that FIG. 2 shows an enlarged view of Portion A in FIG. 1A.

Figure 1:
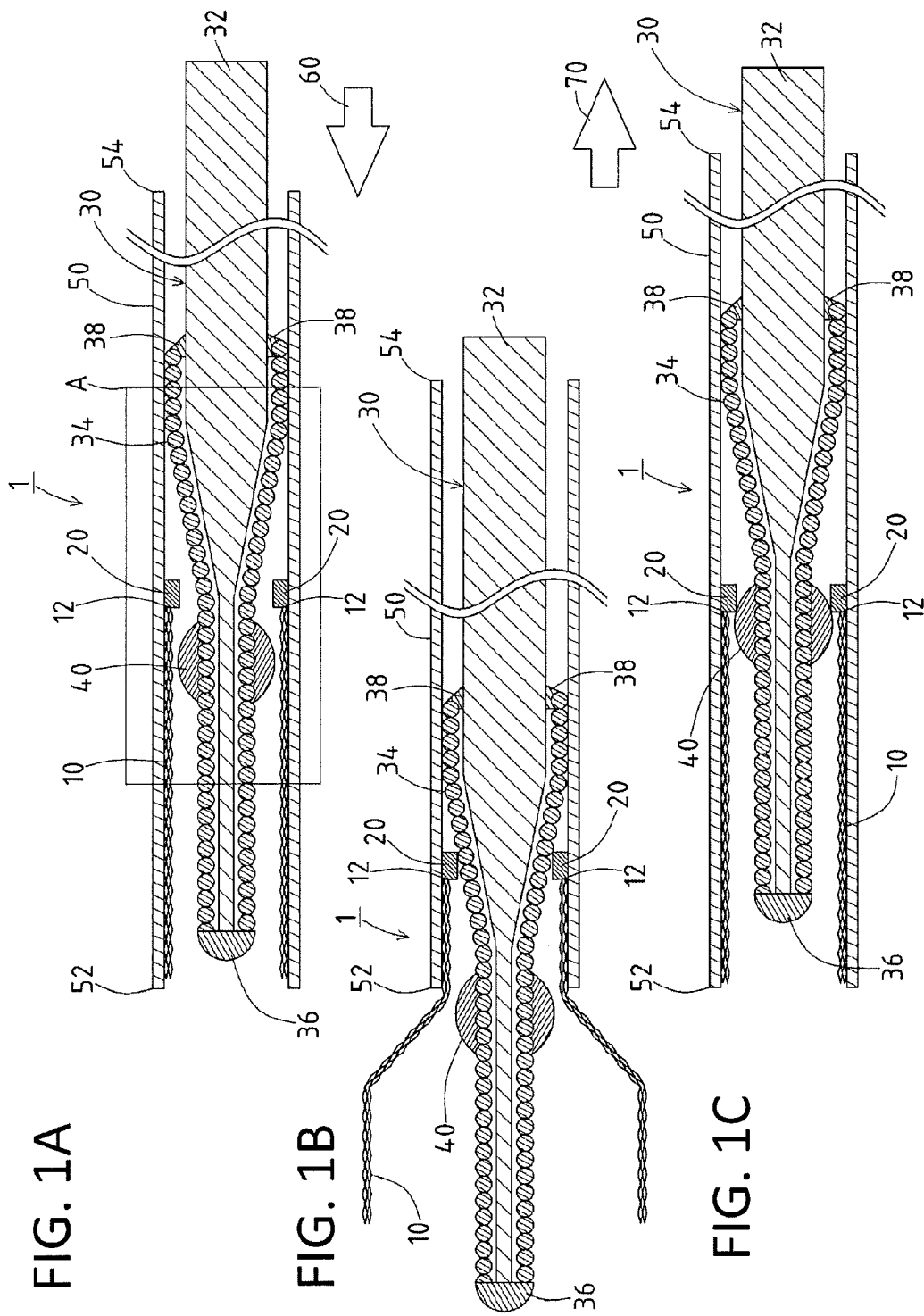
FIG. 1A shows a state in which the stent is stored inside the catheter.
FIG. 1B shows a state in which the pusher guide wire is pushed in the distal direction to release the stent from the distal end of the catheter.
FIG. 1C shows a state in which the pusher guide wire is pulled back in the proximal direction to retract the stent into the catheter.
Figure 2:
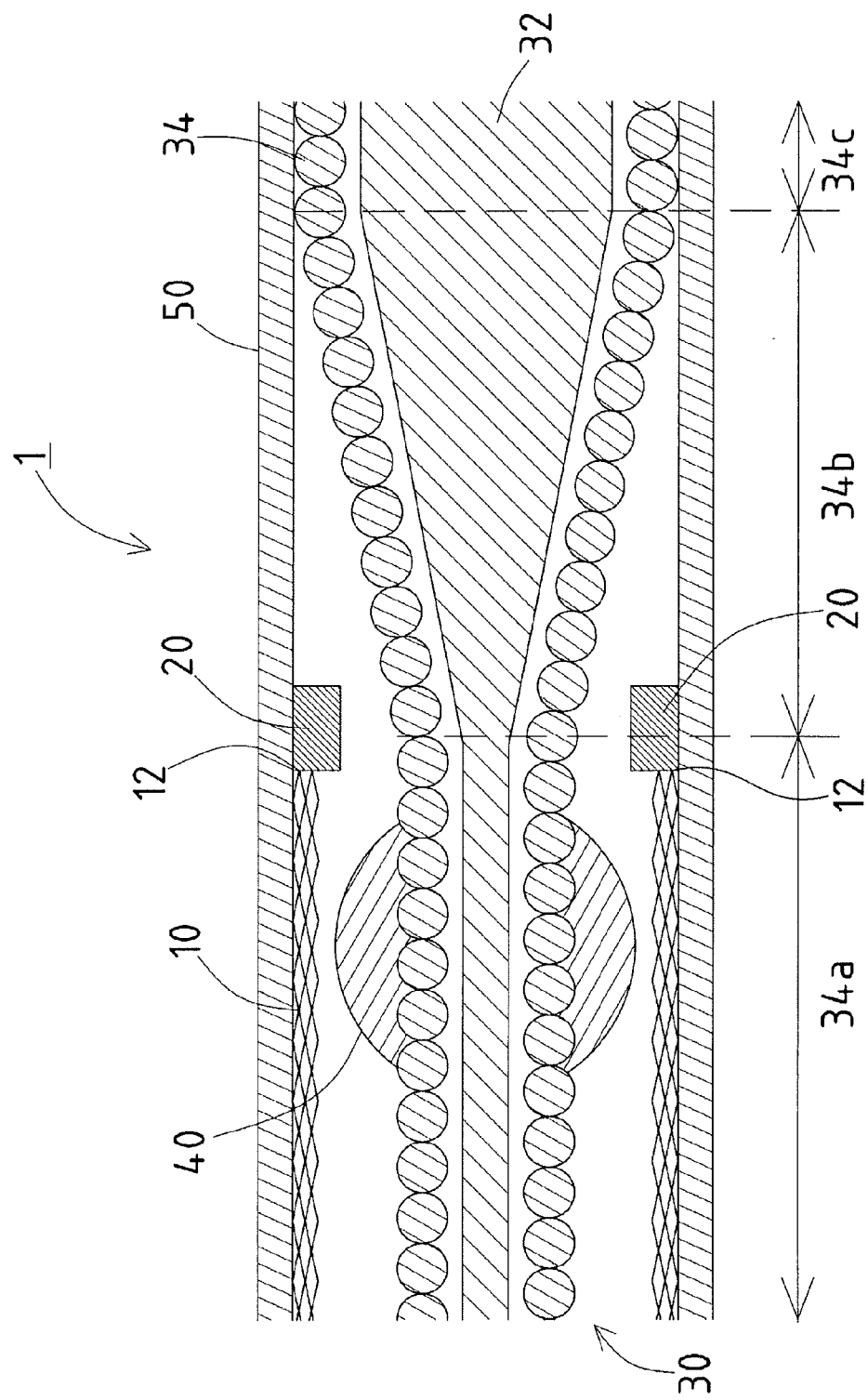
FIG. 2 shows an enlarged view of Portion A in FIG. 1A.

As shown in FIG. 1A, a stent delivery system 1 for delivering a stent 10 to a target site with a pusher guide wire 30 comprises the stent 10, the pusher guide wire 30, and a catheter 50.

Publicly known stents can be used for the stent 10. For example, any of the following can be used: stents in which multiple wires are interwoven into a web-like structure (a mesh-like structure); and stents in which multiple struts (wavy annular bodies) are axially arranged, and adjacent struts are connected via a connecting region. Moreover, a bare metal stent with no drug applied on a surface thereof, as well as a drug-elution stent (DES) with a drug applied on a surface thereof, can be used as the stent 10.

The stent 10 may be formed with metal wires. For example, stainless steel, W, Pt, a Pt—Ni alloy, a Co—Cr alloy, a Ni—Ti alloy, a Cu—Al—Ni alloy and the like can be used for the metal wires. However, the stent 10 may be formed with a resin material such as polyester, polyurethane, polyolefin, polytetrafluoroethylene, a silicon resin and the like instead of only metal wires.

An anchor member 20 is attached to a proximal end 12 of the stent 10. The anchor member 20 prevents the stent 10 from moving anteroposteriorly from the target site or rotating in a radial direction upon making contact with a blood vessel wall or a digestive organ wall when the stent 10 is expanded at the target site. The anchor member 20 comprises a hollow cylinder body such as a ring or a coil body.

The pusher guide wire 30 comprises a core shaft 32, a coil body 34 covering a distal portion of the core shaft 32, a distal end joining portion 36 joining a distal end of the core shaft 32 with a distal end of the coil body 34, a proximal end joining portion 38 joining a proximal end of the coil body 34 with the core shaft 32, and a protruded portion 40 fixed to an outer periphery of the coil body 34 and that is capable of contacting the anchor member 20 of the stent 10.

As shown in FIG. 2, the coil body 34 comprises a small diameter portion 34a having a small outer diameter, a tapered portion 34b having an outer diameter that decreases toward the distal end (toward the left in FIG. 2) and a large diameter portion 34c having a large outer diameter (that is, an outer diameter that is larger than the outer diameter of the small diameter portion). The small diameter portion 34a and the large diameter portion 34c are coil bodies each having a substantially constant outer diameter. The protruded portion 40 is positioned distal to the tapered portion 34b of the coil body 34, and is fixed to the outer periphery of the small diameter portion 34a of the coil body 34. Therefore, the anchor member 20 of the stent 10 is positioned between the tapered portion 34b of the coil body 34 and the protruded portion 40 of the coil body.

Again, as shown in FIG. 1A, the catheter 50 is a hollow cylinder body into which the pusher guide wire 30 can be inserted. The stent 10 can be released from a distal end opening 52 of the catheter 50 to the target site by inserting the pusher guide wire 30 holding the stent 10 through a proximal end opening 54 of the catheter 50, and pushing the core shaft 32 in the distal direction (in the direction of the arrow 60). Note that any known catheter can be used as the catheter 50.

To deliver the stent 10, an operator inserts the catheter 50 so that the distal end opening 52 of the catheter 50 coincides with the target site. The pusher guide wire 30 is inserted through the proximal end opening 54 of the catheter 50 while the catheter 50 is held so as not to move, and the core shaft 32 is pushed in the distal direction to position the stent 10 near the distal end opening 52 of the catheter 50 (see FIG. 1A). After confirming once again that the distal end opening 52 of the catheter 50 coincides with the target site, the core shaft 32 is pushed further in the distal direction to release the stent 10 to the target site through the distal end opening 52 of the catheter 50 (see FIG. 1B). At this time, the stent 10 can be pushed in the distal direction by contacting the tapered portion 34b of the coil body 34 with the anchor member 20 of the stent 10.

However, when the target site is located in a curved blood vessel or digestive organ, and thus the distal end part of the catheter 50 is bent, the distal end opening 52 of the catheter 50 may move in the distal direction when the core shaft 32 is strongly pushed in the distal direction, and the release position of the stent 10 may deviate from the target site. Further, an operator may notice that the release position of the stent 10 deviates from the target site during the release of the stent 10 from the front end opening 52 of the catheter 50. Moreover, the stent 10 expands in the radial direction and at the same time shortens in the axial direction when released from the distal end opening 52 of the catheter 50. Therefore, the release position of the stent 10 may deviate from the target site when the lumen of a blood vessel or digestive organ is larger than expected. In such a case, it is necessary to pull the stent 10 back into the catheter 50 in the middle of the release process, reposition the catheter 50 so that the distal end opening 52 is better positioned, and perform the procedure again.

Upon noticing that the release position of the stent 10 deviates from the target site, an operator can retract the stent 10 into the catheter 50 in the middle of the release process and perform the procedure again by pulling the core shaft 32 in the proximal direction (in the direction of the arrow 70) and allowing the protruded portion 40 to contact the anchor member 20 of the stent 10 (see FIG. 1C).

As described above, according to the stent delivery system 1, the pusher guide wire 30 comprises the coil body 34 having the tapered portion 34b with an outer diameter that decreases toward the distal end, and the protruded portion 40 that is fixed to the outer periphery of the coil body 34. When the stent 10 is delivered to the target site with the pusher guide wire 30, the anchor member 20 of the stent 10 is positioned between the tapered portion 34b of the coil body 34 and the protruded portion 40. Therefore, the anchor member 20 can be pushed in the distal direction by the tapered portion 34b of the coil body 34 without requiring a separate metal ring for pushing the stent 10 in the distal direction, as in conventional stent delivery systems. As a result, the flexibility of the pusher guide wire 30 can be maintained.

Further, since the coil body 34 extends continuously to the distal end joining portion 36 of the pusher guide wire 30, a rotating force exerted by an operator can be transmitted to the distal end of the pusher guide wire 30. Moreover, the stent 10 can be retracted into the catheter 50 in the middle of the release process by pulling the pusher guide wire 30 in the proximal direction so that the protruded portion 40 contacts the anchor member 20. This reduces the risk that the pusher guide wire 30 will get caught within the catheter 50, even in a case where the stent delivery system 1 is inserted in a curved blood vessel or digestive organ, thus allowing easy release of the stent 10 to the intended target site. Once the anchor member 20 is pushed distally beyond the distal end opening 52 of the catheter 50, such that the stent 10 is completely released from the catheter 50, the anchor member 20 (like the rest of the stent 10) expands radially such that the protruded portion 40 will not contact the anchor member 20 upon retraction of the pusher guide wire 30.

Next, materials for each member constituting the pusher guide wire 30 are described. However, there is no particular limitation for the materials.

The core shaft 32 may be formed with a stainless steel (sus304, sus316 and the like) or a superelastic alloy such as a Ni—Ti alloy.

The coil body 34 may be formed with an wire having a radiopacity. Example wire materials include gold, platinum, tungsten, and alloys comprising these elements. In a case where the coil body 34 is formed with a radiopaque wire, an operator can detect the position of the coil body 34 using radiography imaging. As a result, the position of the stent 10 stored in the catheter 50 can be estimated.

Note that the coil body 34 may be formed with an wire comprising a single wire, or may be formed with a twisted wire in which multiple wires are twisted together. The coil body 34 is preferably formed with a twisted wire since it is superior to a single wire in properties such as flexibility and restorability.

The distal end joining portion 36 and the proximal end joining portion 38 may be formed with a solder material (such as aluminum-alloy solder, silver solder, gold solder, or gold-tin alloy solder).

The protruded portion 40 may be formed with a solder material (such as aluminum-alloy solder, silver solder, gold solder, or gold-tin solder) as in the distal end joining portion 36 and the proximal end joining portion 38. Further, the protruded portion 40 may be formed by covering the outer periphery of the small diameter portion 34a of the coil body 34 with a hollow cylinder body such as a ring or a coil body.

Next, the stent delivery system 1a according to the disclosed embodiments will be described with reference to FIG. 3. Only differences from the stent delivery system 1 shown in FIG. 2 will be described.

According to the stent delivery system 1a, an anchor member 20a attached to a proximal end 12a of a stent 10a is inclined at the same angle X as a tapered portion 34b of the coil body 34 relative to a longitudinal axis L of the core shaft 32. Therefore, when an operator pushes the pusher guide wire 30 in the distal direction (in the direction of the arrow 60), the tapered portion 34b of the coil body 34 can contact a greater surface area of an outer periphery surface 22 of the anchor member 20a. As a result, the stent 10a can be more easily delivered to the target site with the pusher guide wire 30 even in a case where the stent delivery system 1a is inserted into a curved blood vessel or digestive organ.

Figure 3:
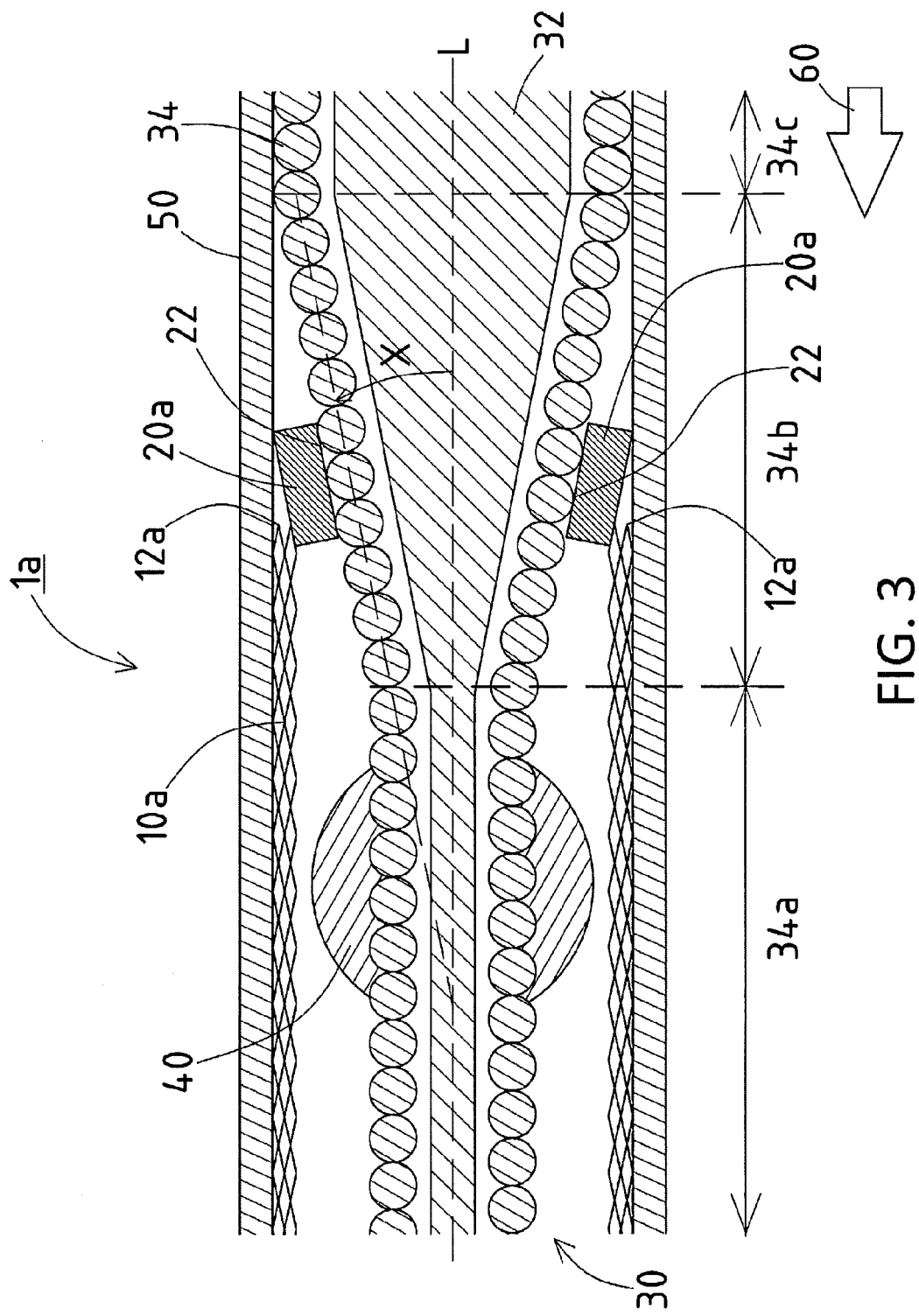
FIG. 3 shows a portion of a stent delivery system according to the disclosed embodiments.

Note that uneven shapes may be formed on the outer periphery surface 22 of the anchor member 20a in order to increase the contact area with the tapered portion 34b of the coil body 34, although this is not shown in FIG. 3.

Next, a stent delivery system 1b according to the disclosed embodiments will be described with reference to FIG. 4. Only differences from the stent delivery system 1a shown in FIG. 3 will be described.

According to the stent delivery system 1b, a pusher guide wire 30a comprises a resin layer 80 on the outer periphery of the tapered portion 34b of the coil body 34. This reduces the risk that the anchor member 20a will get caught between the wires in the tapered portion 34b of the coil body 34 when an operator pushes the pusher guide wire 30a in the distal direction (in the direction of the arrow 60). As a result, the stent 10a can be more reliably delivered to the target site. Further, the stent 10a can be even more easily delivered to the target site by the pusher guide wire 30a even in a case where the stent delivery system 1b is inserted into a curved blood vessel or digestive organ since the contact area between the outer periphery surface 22 of the anchor member 20a and the resin layer 80 can be further increased.

Finally, a stent delivery system 1c according to the disclosed embodiments will be described with reference to FIG. 5. Only differences from the stent delivery system 1 shown in FIG. 1A will be described.

Figure 5:
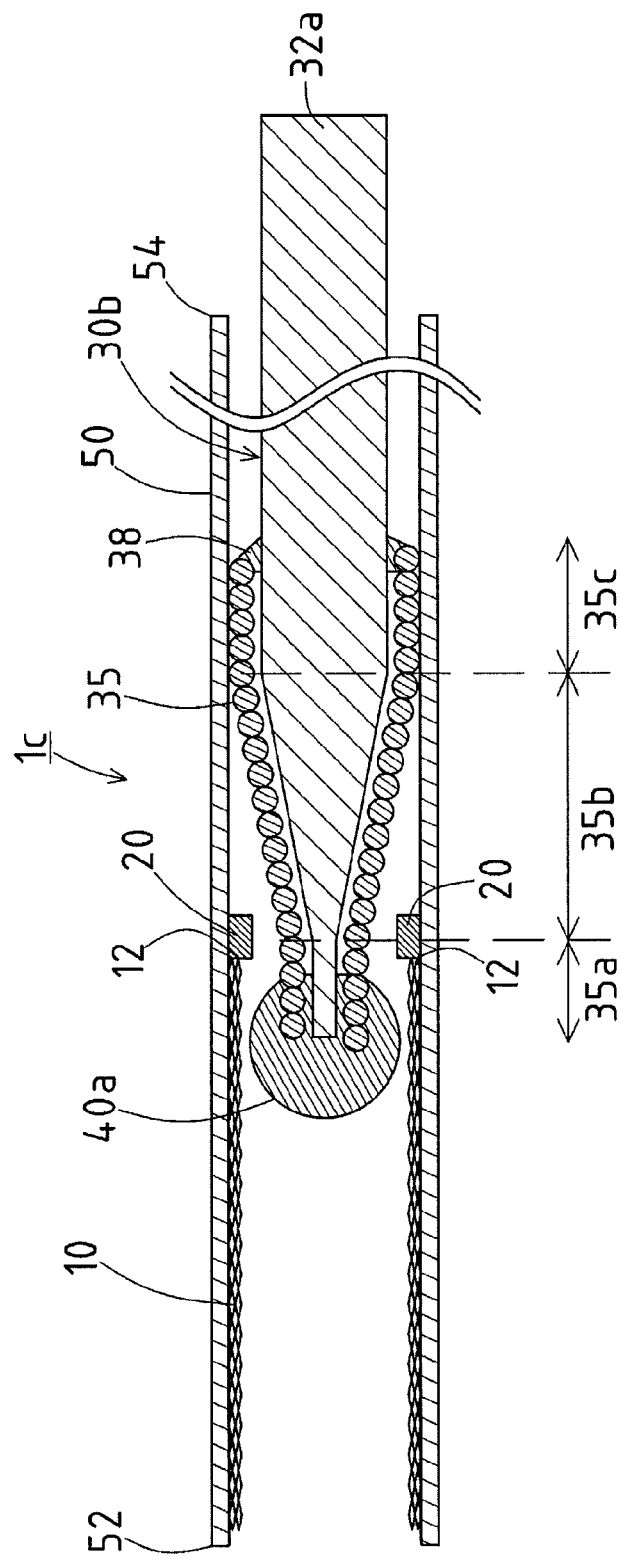
FIG. 5 shows an overall view of a stent delivery system according to the disclosed embodiments.

According to the stent delivery system 1c shown in FIG. 5, a pusher guide wire 30b comprises the core shaft 32a, a coil body 35 covering the distal portion of the core shaft 32a, a protruded portion 40a joining the distal end of the core shaft 32a with a distal end of the coil body 35, and the proximal end joining portion 38 joining a proximal end of the coil body 35 with the core shaft 32a. The coil body 35 comprises a small diameter portion 35a having a small outer diameter, a tapered portion 35b having an outer diameter that decreases toward the distal end (the left side in FIG. 5), and a large diameter portion 35c having a large outer diameter (that is, an outer diameter that is larger than the outer diameter of the small diameter portion).

Unlike the pusher guide wire 30, in the case of the pusher guide wire 30b, the protruded portion 40a functions as a distal end joining portion, and there is no separate distal end joining portion. Therefore, the production of the pusher guide wire 30b is easier because the protruded portion 40a for pulling the stent 10 back into the catheter 50 in the middle of the release process does not need to be fixed to the outer periphery of the small diameter portion 35a of the coil body 35, as in the pusher guide wire 30.

Figure 4:
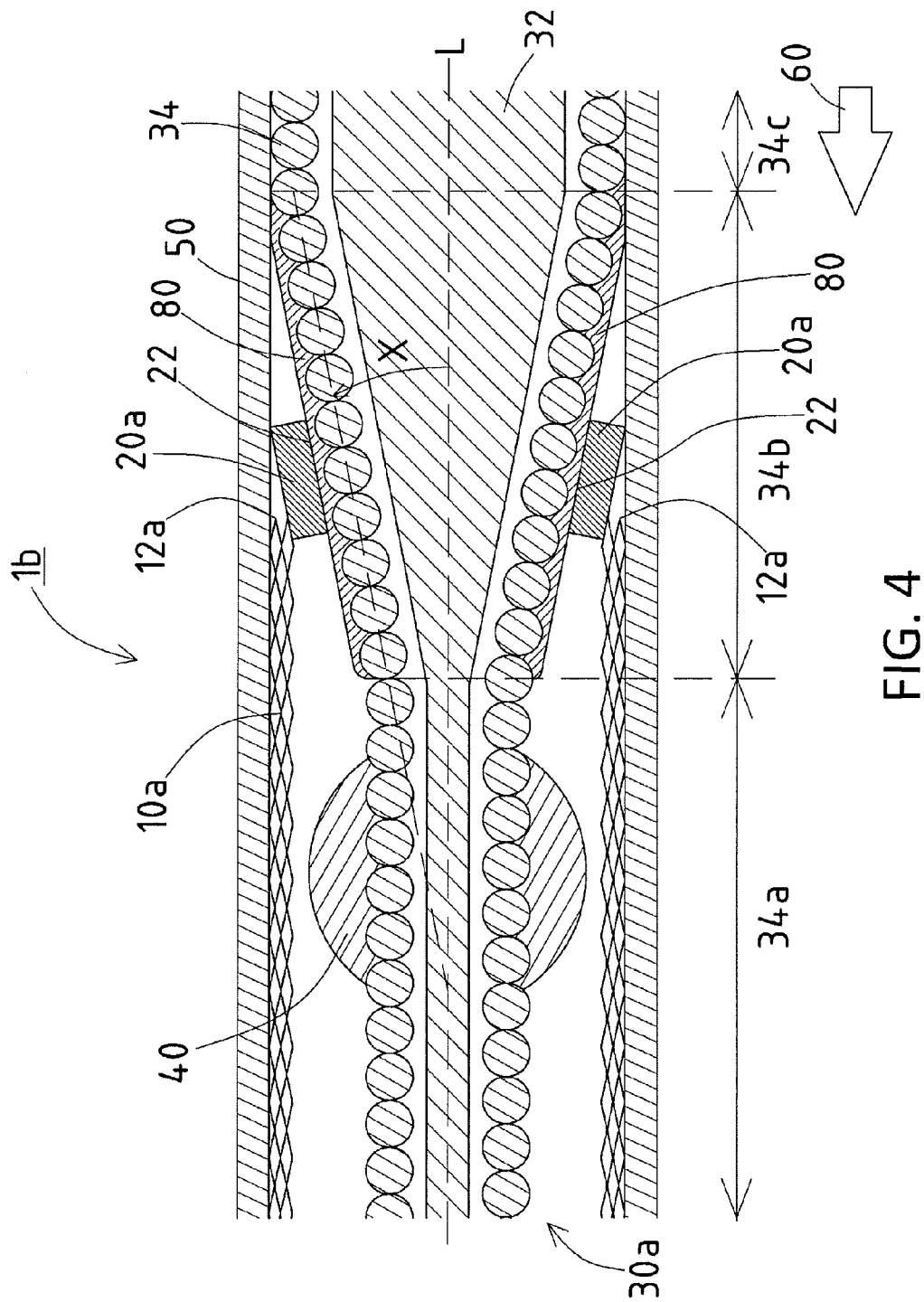
FIG. 4 shows a portion of a stent delivery system according to the disclosed embodiments.

Note that as in the pusher guide wire 30b, the protruded portion 40a, which functions as both a distal end joining portion and a protruded portion, may also be used for the pusher guide wire 30 of the stent delivery system 1a shown in FIG. 3, and the pusher guide wire 30a of the stent delivery system 1b shown in FIG. 4.

Further, although the anchor member 20, 20a is attached only to the proximal end 12, 12a of the stent 10, 10a in the stent delivery system 1, 1a, 1b, 1c described above, the configuration is not particularly limited to this. The anchor member 20, 20a may be attached to a distal portion, a proximal portion, or a medial portion of the stent 10, 10a.

As described above, in the case of the stent delivery system 1, 1a, 1b, 1c, the anchor member 20, 20a can be pushed in the distal direction by the tapered portion 34b, 35b of the coil body 34, 35 since the anchor member 20, 20a of the stent 10, 10a is positioned between the tapered portion 34b, 35b of the coil body 34, 35 and the protruded portion 40, 40a when the stent 10, 10a is delivered to the target site with the pusher guide wire 30, 30a, 30b. Further, a rotating force exerted by an operator can be transmitted to the distal end of the pusher guide wire 30, 30a, 30b since the coil body 34, 35 extends continuously to the distal end joining portion 36 or the protruded portion 40a of the pusher guide wire 30, 30a, 30b. Furthermore, the stent 10, 10a can be retracted into the catheter 50 in the middle of the release process by pulling the pusher guide wire 30, 30a, 30b in the proximal direction so that the protruded portion 40, 40a to contacts the anchor member 20, 20a.

What is claimed is:

1. A stent delivery system comprising:
   a stent having an anchor member at its proximal end;
   a pusher guide wire comprising:
     a core shaft;
     a coil body disposed around a distal portion of the core shaft and including:
       a tapered portion that has an outer diameter that decreases toward a distal end of the coil body; and
       a cylindrical portion positioned distal to the tapered portion and having a constant outer diameter; and
     a protruded portion fixed to an outer periphery of the cylindrical portion of the coil body and configured to contact the anchor member when the pusher guide wire is pulled in a proximal direction,
   wherein when the stent is delivered with the pusher guide wire:
     the anchor member is positioned between the tapered portion of the coil body and the protruded portion, and
     the anchor member and the tapered portion of the coil body are inclined at a same non-zero angle relative to a longitudinal axis of the core shaft.

2. The stent delivery system according to claim 1, wherein a resin layer is provided on an outer periphery of the tapered portion of the coil body.

3. A stent delivery system comprising:
   a stent having an anchor member at its proximal end;
   a pusher guide wire comprising:
     a core shaft;
     a coil body disposed around a distal portion of the core shaft and including:
       a tapered portion that has an outer diameter that decreases toward a distal end of the coil body; and
       a cylindrical portion positioned distal to the tapered portion and having a constant outer diameter; and
     a protruded portion joining a distal end of the core shaft to the distal end of the coil body, fixed to an outer periphery of the cylindrical portion of the coil body, and configured to contact the anchor member when the pusher guide wire is pulled in a proximal direction,
   wherein when the stent is delivered with the pusher guide wire, the anchor member is positioned between the tapered portion of the coil body and the protruded portion.

4. The stent delivery system according to claim 3, wherein a resin layer is provided on an outer periphery of the tapered portion of the coil body.

5. A stent delivery system comprising:
   a stent having an anchor member at its proximal end;
   a pusher guide wire comprising:
     a core shaft;
     a coil body disposed around a distal portion of the core shaft and including:
       a tapered portion that has an outer diameter that decreases toward a distal end of the coil body; and
       a cylindrical portion positioned distal to the tapered portion and having a constant outer diameter; and
     a protruded portion joining a distal end of the core shaft to the distal end of the coil body and configured to contact the anchor member when the pusher guide wire is pulled in a proximal direction,
   wherein when the stent is delivered with the pusher guide wire:
     the anchor member is positioned between the tapered portion of the coil body and the protruded portion, and
     the anchor member and the tapered portion of the coil body are inclined at a same non-zero angle relative to a longitudinal axis of the core shaft.

6. The stent delivery system according to claim 5, wherein a resin layer is provided on an outer periphery of the tapered portion of the coil body.

* * * * *